United States Patent [19]

Emig et al.

[11] Patent Number: 5,508,449

[45] Date of Patent: Apr. 16, 1996

[54] PROCESS FOR THE PREPARATION OF TRIOXANE

[75] Inventors: Gerhard Emig, Erlangen; Benno Krüger, Waldems-Esch; Frank Kern, Kandel; Michael Hoffmockel, Niedernhausen; Karl-Friedrich Mück; Günter Sextro, both of Wiesbaden, all of Germany

[73] Assignee: Hoechst Aktiengesellschaft

[21] Appl. No.: 178,129

[22] Filed: Jan. 6, 1994

[30] Foreign Application Priority Data

Jan. 6, 1993 [DE] Germany ............... 43 00 138.6

[51] Int. Cl.[6] ............................................. C07D 323/06
[52] U.S. Cl. ............................................................ 549/368
[58] Field of Search ................................................ 549/368

[56] References Cited

U.S. PATENT DOCUMENTS 3,496,192  2/1970  Ackermann et al. ............... 549/368
4,381,397  4/1983  Yoshida et al. ..................... 549/368
4,563,536  1/1986  Yoshida et al. ..................... 549/368

FOREIGN PATENT DOCUMENTS 3106476  12/1981  Germany.

Primary Examiner—C. Warren Ivy
Assistant Examiner—Raymond Covington
Attorney, Agent, or Firm—Connolly & Hutz

[57] ABSTRACT

In a process for the preparation of trioxane from formaldehyde in the gas phase in the presence of a catalyst, the catalyst employed is 11-molybdo-1-vanadophosphoric acid, $H_4PVMo_{11}O_{40} \cdot n\, H_2O$ (n=0–32).

Advantages of this process are, inter alia, high space-time yields and the suppression of byproducts.

15 Claims, 1 Drawing Sheet

PROCESS FOR THE PREPARATION OF TRIOXANE

The invention relates to a process for the continuous preparation of trioxane in the gas phase by heterogeneous catalysis using 11-molybdo-1-vanadophosphoric acid, $H_4PVMo_{11}O_{40} \cdot n\, H_2O$ (n=0–32) (hereinafter referred to as 1-V acid) as catalyst.

Trioxane can be prepared from aqueous formaldehyde solutions using acid catalysts. A characteristic of these processes is the high energy consumption for vaporization of water which is introduced into the process by the feedstock streams. There are various proposals for preparing trioxane by gas-phase trimerization of formaldehyde, but these always use formaldehyde streams with various water contents. Working with water-containing formaldehyde leads to problems caused by deposits of polyoxymethylene on the catalyst surface. A process for the preparation of trioxane by means of an acid ion exchange resin is known (DE-C-1 593 990). Likewise known is a catalyst for the gas-phase trimerization in the form of phosphoric acid and sulfuric acid on $SiO_2$ supports (AT-B 252 913). Various heteropolyacids have already been used as catalysts in the gas-phase trimerization of formaldehyde (JP-A 59-25387). However, the yields are not satisfactory.

The object of the invention was to overcome said disadvantages.

The object was achieved by a process which is distinguished from the prior processes by the catalyst, the composition of the feedstock stream and the high selectivity of the catalyst, particularly at high partial pressures of formaldehyde.

The invention thus provides a process for the preparation of trioxane from formaldehyde in the gas phase in the presence of a catalyst, wherein the catalyst employed is 11-molybdo-1-vanadophosphoric acid, $H_4PVMo_{11}O_{40} \cdot n\, H_2O$ (n=0–32).

BRIEF DESCRIPTION OF THE DRAWING

The sole FIGURE of the Drawing illustrates an apparatus suitable for carrying out the process of this invention.

DETAILED DESCRIPTION

Figure 1:
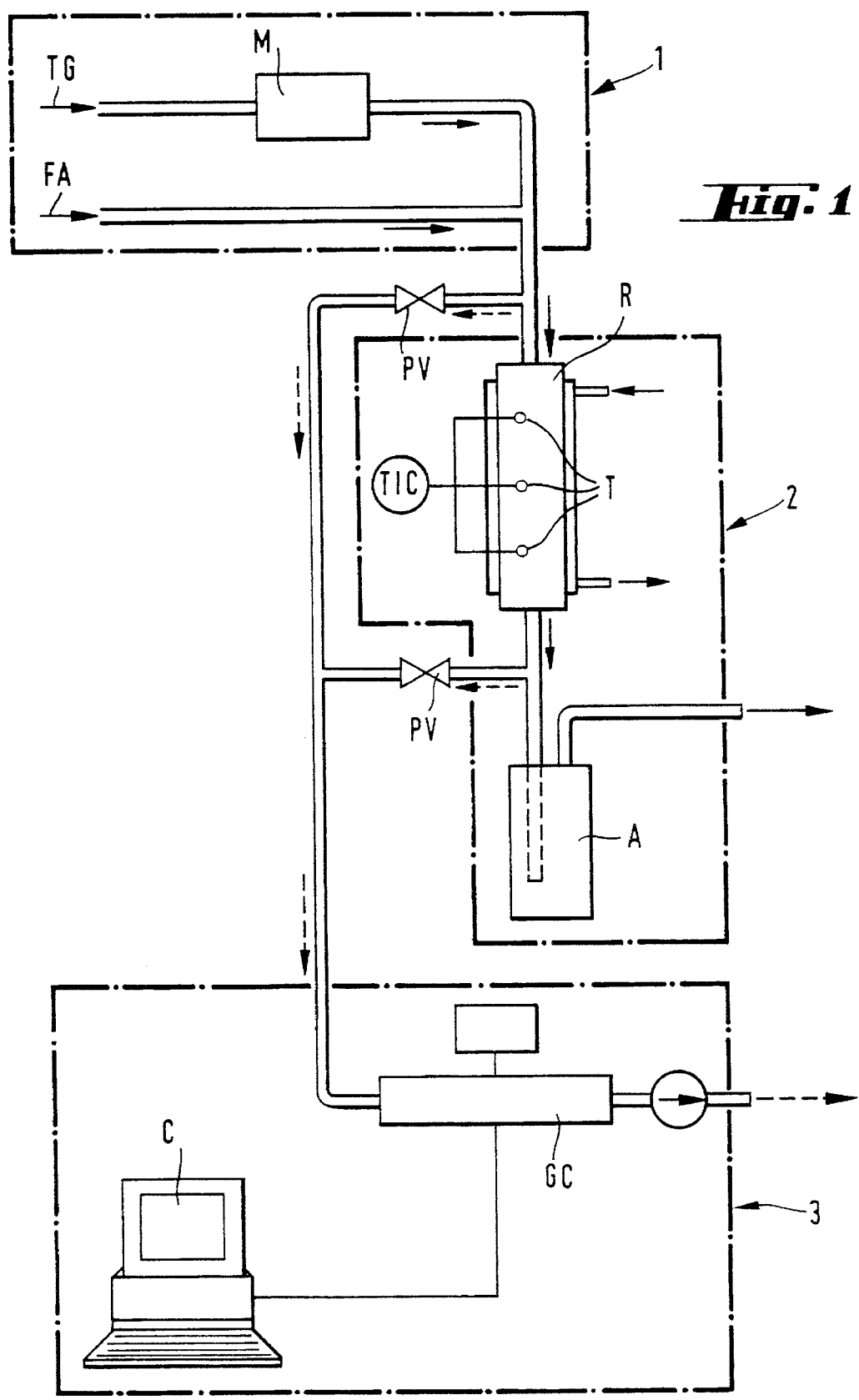

Inert materials, for example pellets of silicon carbide, silicon dioxide or aluminum oxide, can be employed as supports for the catalytic substance.

The pressing aids used are materials which are inert in the reaction, for example finely divided silica ($SiO_2$), aluminum oxide or hydroxide.

If the gas stream employed does not contain water, the catalyst is in anhydrous form under the reaction conditions.

The following advantages of the process warrant particular emphasis:

1. Achievement of high space-time yields (STY) [kg/m$^3$·h]
2. No byproducts
3. Moderate evolution of heat in the synthesis reactor The catalyst is generally employed as such. However, the use of supports or pressing aids is advantageous.

Generally, formaldehyde having a residual water content of <50 ppm is used, this being described as anhydrous formaldehyde. However, the formaldehyde which can be employed in the process may also have a low water content, i.e. the gas stream fed into the reactor may contain up to 1% by weight of water. If a higher water content is employed, the STY is considerably increased, with the percentage conversion of formaldehyde likewise increasing.

The temperature range for the reaction is from 80° C. to 150° C. Preference is given to the range from 100° C. to 120° C.

The contact duration over which no byproducts occur in the process is generally from 1 to 30 seconds, preferably from 1 to 10 seconds. Longer residence times are possible, but there is then the danger of forming byproducts.

The reaction is affected by the partial pressure of formaldehyde. The catalyst has high selectivity for the formation of trioxane over a wide pressure range. The partial pressure of formaldehyde at the inlet is generally from 0.5 to 5 bar, preferably from 0.5 to 2 bar.

The apparatus for the preparation of trioxane according to the invention comprised three parts (see FIG. 1):

1. Metering
2. Formation reactor
3. Analysis

To carry out a test, formaldehyde (FA) (=feedstock stream) is introduced into the apparatus and, if desired, mixed with a carrier gas. Suitable carrier gases are the noble gases helium, argon, krypton or xenon, but nitrogen is preferred.

The formation reactor (R) comprised, for the present experiments 1 to 4, a stainless-steel tube reactor having a length of 150 mm and a diameter of 30 mm. Supply and removal of heat were regulated by a thermostat (TIC), silicone oil was used as heat transfer medium. The use of heat transfer media such as mineral oils is likewise possible. The temperature in the reactor was measured radially at three different points (T) along the reactor. These temperatures were recorded during the tests and provided information about the stable operating condition of the reactor over the test duration. The outlet stream leaving the reactor and containing the reaction products formed was trapped in water in an absorption device (A). The trioxane formed can be isolated therefrom by extraction in a known manner.

The quantitative tests of the formation of trioxane in the gas phase were carried out using on-line analysis. Samples were taken at two different points on the apparatus during operation and analyzed in a gas chromatograph (GC).

The arrangement of the apparatus for the process according to the invention and also its dimensions can naturally be adapted to the prevailing conditions.

For experiments 5 and 6, the dimensions of the reactor used were altered. Here the length was 130 mm and the diameter was 10 mm.

Experiment description:

Individual parameters which were varied are indicated in the individual exhales.

Anhydrous formaldehyde was employed in the experiments 1 to 4.

A carrier gas (CG), preferably nitrogen, can be added to the feedstock stream (FA) with the aid of a mass flow regulator (M). However, it is also possible to work without carrier gas. The flow rate of the feedstock stream can be varied, for example increased, and the residence time in the reactor (R) thereby affected, for example lowered, by use of a carrier gas. Various amounts of catalyst were tested in the reactor (R). The gas composition upstream and downstream of the reactor (R) was determined on-line using a gas chromatograph (GC). The conversion was calculated from the compositions of the gases. The temperature was regulated via a thermostat (TIC) and measured at three different points (T) along the catalyst bed.

Sampling for analysis of the inlet and outlet streams was carried out automatically and at regular intervals, for example every seven minutes, the isolation devices (PV) (pneumatic ball valves) being connected to a gas chromatograph (GC) which is controlled by a computer (Comp.). The values in the tables of the examples are explained below:

The mole fraction $X_{form}$ is based on the gas composition at the inlet of the synthesis reactor. It is calculated according to equation (1).

$$X_{form} = n^\circ_{form}/n_{tot} = N^\circ_{form}/(n^\circ_{form} + n_{N2}) \quad (1)$$

$n^\circ_{form}$: formaldehyde flow rate at the inlet [mol/h]

$n_{tot}$: total flow rate [mol/h]

$n_{N2}$: nitrogen flow rate [mol/h]

The experimentally determined conversion $C_{exp}$ is calculated according to equation (2).

$$C_{exp} = (n^\circ_{form} - n_{form})/n^\circ_{form} \cdot 100 \quad (2)$$

$n^\circ_{form}$: formaldehyde flow rate at the inlet [mol/h]

$n_{form}$: formaldehyde flow rate at the outlet [mol/h]

The relative conversion $C_{rel}$ (equation (3)) is the ratio of the experimentally determined conversion $C_{exp}$ and the equilibrium conversion $C_{eq}$, determined from the equilibrium constants according to Busfield and Merigold, ("The Gas-Phase Equilibrium between Trioxane and Formaldehyde", J. Chem. Soc (A), 1969 p. 2975).

$$C_{rel} = C_{exp}/C_{eq} \cdot 100 \quad (3)$$

$C_{exp}$: experimental conversion [%]

$C_{eq}$: equilibrium conversion [%]

Catalyst preparation:

To prepare the generally cylindrical supported catalysts, the 1-V acid, $H_4PVMo_{11}O_{40} \cdot n\ H_2O$ (n=0–32), is dissolved in water and used for impregnating the supports. For this purpose, the catalyst supports are coated with the solution, the air contained in the pores of the supports is removed by reducing the pressure in the impregnating vessel, the supernatant solution is poured off and the impregnated supports are dried in air at 373K. If the supports are only to be impregnated, the evacuation can be omitted. Unsupported catalysts are prepared by mixing sieved 1-V acid, particle size 150 μm, with the desired amount of pressing aid and subsequently pressing into pellets of the desired size, for example in cylindrical form. The catalyst of Example 2 was prepared by, for example, dissolving 3.8 g of 1-V acid in 60 cm³ of distilled water and treating the support of silicon carbide as described above. This method gives pellets which contain an amount of 1.69 g of 1-V acid in a 50 cm³ catalyst bed.

EXAMPLES 1) 61.25 g of the 1-V acid catalyst containing 30% of $SiO_2$ as pressing aid were employed in the form of cylindrical pellets (diameter 5 mm, length 5 mm) in the reactor R. The volume of the catalyst bed was 56.2 cm³. The following conversions were achieved with a selectivity of 1, i.e. no byproducts were obtained. The total pressure was 1.050 bar.

TABLE 1

| Conversions at various temperatures | | | | | | |
|---|---|---|---|---|---|---|
| Temp. [K.] | Residence time [s] | n°$_{form}$ [mol/h] | Mole fraction | $C_{exp}$ [%] | $C_{rel}$ [%] | STY [kg/m³h] |
| 358 | 3.4 | 0.692 | 0.267 | 32.03 | 100 | 118.5 |
| 363 | 4.6 | 0.962 | 0.492 | 35.2 | 87.5 | 180.96 |
| 368 | 3.6 | 1.54 | 0.611 | 40.2 | 88.9 | 329.89 |

2) 1.69 g of the 1-V acid catalyst on 46.15 g of cylindrical SiC pellets (diameter 6 mm, length 6 mm) were employed in the reactor R. The following conversions were achieved with a selectivity of 1. The partial pressure of formaldehyde at the inlet was 1075 mbar, the volume of the catalyst bed was 50 cm³.

TABLE 2

| Conversions at various temperatures | | | | | | |
|---|---|---|---|---|---|---|
| Temp. [K.] | Residence time [s] | n°$_{form}$ [mol/h] | Mole fraction | $C_{exp}$ [%] | $C_{rel}$ [%] | STY [kg/m³h] |
| 383 | 11.25 | 0.516 | 0.6 | 17.1 | 50.6 | 53.0 |
| 380.5 | 11.25 | 0.516 | 0.6 | 29.2 | 76.8 | 90.5 |
| 378 | 11.25 | 0.517 | 0.6 | 33.76 | 79.4 | 104.8 |

3) 0.563 g of the 1-V acid catalyst on 16.7 g of cylindrical SiC pellets (diameter 6 mm, length 6 mm) were employed in the reactor R. The following conversions were achieved with a selectivity of 1. The partial pressure of formaldehyde at the inlet was 1150 mbar, the volume of the catalyst bed was 16.6 cm³.

TABLE 3

| Conversions at various temperatures | | | | | | |
|---|---|---|---|---|---|---|
| Temp. [K.] | Residence time [s] | n°$_{form}$ [mol/h] | Mole fraction | $C_{exp}$ [%] | $C_{rel}$ [%] | STY [kg/m³h] |
| 383 | 5.1 | 0.386 | 0.6 | 29.6 | 81.3 | 206.8 |
| 380.5 | 5.1 | 0.378 | 0.6 | 35.2 | 82.4 | 240.8 |

4) 0.9 g of the 1-V acid catalyst on 26.65 g of cylindrical SiC pellets (diameter 6 mm, length 6 mm) were employed in the reactor R. The following conversions were achieved with a selectivity of 1. The partial pressure of formaldehyde at the inlet was 950 mbar, the volume of the catalyst bed was 26.7 cm³.

TABLE 4

| Conversions at various temperatures | | | | | | |
|---|---|---|---|---|---|---|
| Temp. [K.] | Residence time [s] | n°$_{form}$ [mol/h] | Mole fraction | $C_{exp}$ [%] | $C_{rel}$ [%] | STY [kg/m³h] |
| 383 | 5.1 | 0.375 | 0.6 | 13.67 | 45.5 | 57.6 |
| 380.5 | 5.1 | 0.374 | 0.6 | 17.2 | 48.8 | 72.4 |
| 378 | 5.1 | 0.375 | 0.6 | 21.9 | 56.6 | 92.3 |
| 375.5 | 5.1 | 0.374 | 0.6 | 22.51 | 52.1 | 94.8 |

Examples 1 to 4 show that the catalyst possesses high selectivity for the formation of trioxane. The activity of the catalyst rises with increasing partial pressure of formaldehyde and decreasing reactor temperature. Both high conversions close to the equilibrium conversion and also high space-time yields can be achieved. In all the examples shown, nitrogen was employed as carrier gas and as reference gas for the analyses.

In Examples 1 to 4, the water content of the formaldehyde inlet stream was less 50 ppm.

In each case, the catalysts used showed no sign of deactivation after a test duration of 300 hours.

The use of anhydrous formaldehyde allows the use of higher partial pressures of formaldehyde at the inlet than with water-containing formaldehyde.

The decomposition pressure of paraformaldehyde containing 5% of water is, for example, 0.97 bar at a temperature of 380.5K. In Example 3, the use of anhydrous formaldehyde allowed the partial pressure of formaldehyde at the inlet to be increased to 1.15 bar at this temperature without condensation of formaldehyde occurring in the reactor. The increase in the inlet partial pressure is associated with a significant increase in the maximum possible equilibrium conversion from 35% to 40% and thus in the economics of the process.

Examples 5 and 6 below describe the positive effect of a certain water content in the reaction gas (Example 5) compared with an anhydrous batch (Example 6). The reactor as in FIG. 1 had a length of 130 mm and a diameter of 10 mm. The water content was 1% by weight, the stream of nitrogen (CG) being laden with this amount.

In two successive experiments, an inlet stream was passed over the catalyst bed under the conditions shown in Table 5.

TABLE 5

|  | Example 5 | Example 6 (comparison) |
|---|---|---|
| Total pressure [mbar] | 1120 | 1120 |
| Partial pressure of $N^2$ [mbar] | 183 | 200 |
| Partial pressure of $H_2O$ [mbar] | 17 | 0 |
| Partial pressure of $CH_2O$ [mbar] | 920 | 920 |
| Reactor temperature [°C.] | 110 | 110 |
| Catalyst [mg] $H_4PVMO^{11}O_{40}$ | 85 on 10 cm$^3$ of cylindrical SiC pellets, 1 × 1 mm | 85 on 10 cm$^3$ of cylindrical SiC pellets, 1 × 1 mm |
| Reaction volume [cm$^3$] | 10 | 10 |
| n°$_{form}$ [mol/l] | 0.22 | 0.22 |
| $C_{exp}$ ($CH_2O$) [%] | 12 | 7.5 |
| STY [kg/m$^3$/·h] | 84 | 50 |

The product mixture at the reactor outlet comprised formaldehyde, water, nitrogen and trioxane, the trioxane being obtained with a selectivity of 1.

The inlet and outlet streams were analyzed by gas chromatography (FIG. 1). The activity of the catalyst is considerably increased by the water content of the inlet stream.

What is claimed is:

1. A process for the preparation of trioxane, comprising:
    bringing formaldehyde in the gas phase into contact with a catalyst comprising 11-molybdo-1-vanadophosphoric acid, $H_4PVMo_{11}O_{40} \cdot n\ H_2O$, where n is a number from 0 to 32.

2. The process as claimed in claim 1, wherein said catalyst has been applied to an inert support material or has been pressed with an inert pressing aid.

3. The process as claimed in claim 2, wherein said inert support material is silicon carbide, and said pressing aid is finely divided silica.

4. The process as claimed in claim 1, wherein the formaldehyde in the gas phase is essentially anhydrous.

5. The process as claimed in claim 1, wherein the formaldehyde in the gas phase has a water content not exceeding 1% by weight.

6. The process as claimed in claim 1, wherein the formaldehyde is brought into contact with said catalyst at a temperature in the range of 80° to 150° C.

7. The process as claimed in claim 6, wherein said temperature is in the range of 100° to 120° C.

8. The process as claimed in claim 1, wherein the duration of the contact between the formaldehyde and the catalyst is from 1 to 30 seconds.

9. The process as claimed in claim 8, wherein said duration is from 1 to 10 seconds.

10. The process as claimed in claim 1, wherein the formaldehyde is brought into contact with said catalyst in a reaction zone having an inlet, and wherein the partial pressure of the formaldehyde at the inlet is from 0.5 to 5 bar.

11. The process as claimed in claim 10, wherein said partial pressure is from 0.5 to 2 bar.

12. The process as claimed in claim 1, wherein the formaldehyde is brought into contact with said catalyst in the presence of a carrier gas.

13. The process as claimed in claim 12, wherein the carrier gas is nitrogen.

14. The process as claimed in claim 1, wherein the formaldehyde is brought into contact with said catalyst in a reaction zone having an inlet and an outlet; the gases from the outlet containing the reaction products are conveyed to a water-containing absorption zone wherein the reaction products are trapped in water, and the trioxane is recovered from the water in the absorption zone by extraction.

15. An apparatus for the production of trioxane from formaldehyde comprising a reaction zone having an inlet and an outlet and containing a catalyst for the conversion of formaldehyde to trioxane, said outlet being in communication with an absorption zone, and said catalyst comprising the compound 11-molybdo- 1-vanadophosphoric acid, $H_4PVMo_{11}O_{40} \cdot n\ H_2O$, where n is a number from 0 to 32.

* * * * *